United States Patent [19]

Murofushi et al.

[11] Patent Number: 5,595,892

[45] Date of Patent: Jan. 21, 1997

[54] PROCESS FOR PREPARATION OF PURIFIED XANTHAN GUM

[75] Inventors: Kanji Murofushi; Taira Homma, both of Joetsu; Shigehiro Nagura, Niigata-ken, all of Japan; Richard W. Armentrout, La Jolla, Calif.

[73] Assignees: Shin-Etsu Chemical Co., Ltd., Tokyo, Japan; Shin-Etsu Bio, Inc., San Diego, Calif.

[21] Appl. No.: 345,076

[22] Filed: Nov. 28, 1994

Related U.S. Application Data

[63] Continuation-in-part of Ser. No. 990,758, Dec. 15, 1992.

[30] Foreign Application Priority Data

Dec. 20, 1991 [JP] Japan ................................ 3-338244
Mar. 13, 1992 [JP] Japan ................................ 4-054898

[51] Int. Cl.⁶ .......................... A01N 63/00; C12P 19/06; C12P 19/12
[52] U.S. Cl. .................... 435/104; 435/100; 435/252.1; 435/262; 435/822; 435/910; 424/93.4
[58] Field of Search ................... 435/100, 104, 435/252.1, 262, 822, 910; 424/93.4

[56] References Cited

U.S. PATENT DOCUMENTS

| | | | |
|---|---|---|---|
| 3,054,689 | 9/1962 | Jeanes et al. | 106/208 |
| 3,096,293 | 7/1963 | Jeanes et al. | 252/316 |
| 3,119,812 | 1/1964 | Rogovin et al. | 260/209 |
| 3,163,602 | 12/1964 | Lindblom et al. | 252/8.55 |
| 3,251,768 | 5/1966 | Walker | 252/8.5 |
| 3,288,211 | 11/1966 | Johnston | 166/9 |
| 3,305,016 | 2/1967 | Lindblom et al. | 166/9 |
| 3,342,732 | 9/1967 | Goetz | 210/54 |
| 3,382,229 | 5/1968 | Patton et al. | 260/209 |
| 3,516,983 | 6/1970 | Colegrove | 260/209 |
| 3,591,578 | 7/1971 | Colin et al. | 360/209 |
| 3,729,460 | 4/1973 | Patton | 260/209 |
| 3,838,009 | 9/1974 | Fukumoto et al. | 195/6 S |
| 3,862,003 | 1/1975 | Okuyama et al. | 195/7 |
| 3,964,972 | 6/1976 | Patton | 195/31 P |
| 3,966,618 | 6/1976 | Colegrove | 252/855 D |
| 4,010,071 | 3/1977 | Colegrove | 195/7 |
| 4,032,663 | 6/1977 | Kobayashi et al. | 426/51 |
| 4,094,739 | 6/1978 | Schroeck | 195/7 |
| 4,135,979 | 1/1979 | Corley et al. | 195/31 |
| 4,165,257 | 8/1979 | Stokke | 435/262 |
| 4,299,825 | 11/1981 | Lee | 424/180 |
| 4,416,990 | 11/1983 | Rinaudo et al. | 435/104 |
| 4,431,734 | 2/1984 | Rinaudo et al. | 435/104 |
| 4,567,140 | 1/1986 | Voelskow et al. | 435/42 |
| 4,720,389 | 1/1988 | Clare et al. | 426/329 |
| 4,729,900 | 3/1988 | Clare et al. | 426/329 |
| 4,729,958 | 3/1988 | Drozd et al. | 435/270 |
| 4,775,632 | 10/1988 | Gozard et al. | 435/104 |
| 4,904,586 | 2/1990 | Ballerini et al. | 435/114 |
| 5,079,348 | 1/1992 | Clare et al. | 536/3 |
| 5,153,317 | 10/1992 | Ortega et al. | 8/543 |
| 5,493,015 | 2/1996 | Murofushi et al. | 536/127 |

FOREIGN PATENT DOCUMENTS

| | | | |
|---|---|---|---|
| 1038781 | 9/1978 | Canada | 195/140 |
| 1117410 | 2/1982 | Canada | 166/32 |
| 1172589 | 8/1984 | Canada | 195/86 |
| 1174993 | 9/1984 | Canada | 195/68 |
| 1280988 | 4/1987 | Canada | 195/140 |
| 1244368 | 11/1988 | Canada | 195/140 |
| 1288714 | 11/1989 | Canada | 195/73 |
| 2606423 | 5/1988 | France | 435/104 |
| 0129802 | 2/1978 | Germany | 435/104 |
| 2060597 | 3/1990 | Japan | 435/104 |
| 2085904 | 5/1982 | United Kingdom | 435/104 |
| 2099008 | 12/1982 | United Kingdom | 435/104 |

*Primary Examiner*—Michael G. Wityshyn
*Assistant Examiner*—Deborah K. Ware
*Attorney, Agent, or Firm*—McAulay Fisher Nissen Goldberg & Kiel, LLP

[57] ABSTRACT

The process includes heat-treating a xanthan gum fermented broth, and consecutively treating the broth first with alkaline protease and then with lysozyme or in reverse order, and thereafter recovering xanthan gum from the treated broth. A clear aqueous solution of xanthan gum may be obtained without complex procedures.

8 Claims, No Drawings

PROCESS FOR PREPARATION OF PURIFIED XANTHAN GUM

CROSS-REFERENCE TO RELATED APPLICATIONS

This application is a continuation-in-part of application Ser. No. 07/990,758, filed Dec. 15, 1992, the contents of which are hereby incorporated by reference.

BACKGROUND OF THE INVENTION

1. Field of the Invention

The present invention relates to a process for the preparation of purified xanthan gum. More particularly, it is directed to a process for the improvement of the transparency of a fermentation broth containing dissolved xanthan gum as well as aqueous solutions of xanthan gum by enzymatic treatment of the broth or aqueous solution.

2. Description of the Related Art

Xanthan gum can be obtained by conventional fermentation of a xanthan gum-producing bacterium, e.g., Xanthomonas campestris, a species in the genus Xanthomonas, and the like. It is recovered by precipitation with isopropanol from a fermented broth (This compound and process for preparing it are described in U.S. Pat. No. 3,659,026, column 4.)

Other processes for the manufacture of xanthan gum use, in place of *Xanthomonas campestris*, such other known xanthan gum-producing bacteria as *Xanthomonas carotate, incanae, begoniae, papavericola, translucens, vasculorum,* and *hederae*. All these species can produce a xanthan gum fermented broth.

U.S. Pat. Nos. 5,310,677, 5,194,386 and U.S. patent application Ser. No. 07/826,095, filed Jan. 27, 1992, the contents of each of which are incorporated herein by reference, discloses several hyperproducing strains of *X. campestris* and methods for obtaining these strains. In particular, two strains identified as X50 (ATCC 55429) and X59 (ATCC 55298), each of which is available from the American Type Culture Collection pursuant to Budapest Treaty, have been deposited on Feb. 18, 1992, with the American Type Culture Collection in Rockville, Md., and all restrictions of the availability to the public of the materials so deposited will be irrevocably removed upon the granting of a patent thereon. X50 and X59 are obtained by a selection procedure described in the above U.S. Patents, starting from publicly available strain NRRL 1459 which is referred to as X55. The broth at the end of fermentation of such strains contains from 0.5 to 2 percent by weight of undissolved matter including unconsumed nutrients and bacterial cell residues, in addition to about 2 to 5 percent by weight of xanthan gum. The aqueous solution of xanthan gum separated by extraction from the broth has low transparency. This presents problems in the fields where clear products are required, such as, the food and cosmetic industries, and in applications for secondary recovery of petroleum.

Known methods for the purification and clarification of xanthan gum, and solutions and fermentation broths thereof depend on centrifugation or cake filtration for the removal of the undissolved matter from the broth. In either case, however, the broth as obtained from the fermentation is so viscous that it must be diluted with water which adds to the cost and complexity of the process and makes such methods impractical. A variation of those methods suggests heating of the broth to enhance its filtration properties.

One effective approach is solubilizing the undissolved matter in the broth by enzymatic treatment. Many proposals have hitherto been made in this direction.

For example, (Japanese Patent Provisional Publication (Kokai) No. 50-121493) and U.S. Pat. Nos. 3,966,618/1976, 4,010,071/1977, and 4,165,257/1979 propose clarification by use of alkaline protease and neutral protease. They report, in fact, that xanthan gum solutions cannot necessarily be made absolutely clear or transparent and the solutions retain some degree of turbidity.

European Patent Publication No. EP 78621, British Patent Application No. 8,132,564/1981 (Japanese Patent Kokai No. 58-81792) teaches the use of acidic protease and neutral protease for this purpose. U.S. Pat. No. 4,119,491 (Japanese Patent Kokoku No. 62-44918) teaches bringing a solution that results from protease treatment into contact with a siliceous solid matter and then removing the cellular debris from an aqueous polymer solution. U.S. Pat. No. 4,431,734 (Japanese Patent Kokai No. 57-202303) proposes an enzymatic treatment using polysaccharase and protease. U.S. Pat. 4,904,586 (Japanese Patent Kokai No. 63-287494) teaches the combined use of a polygalacturonase active enzyme and a protease-active enzyme. European Patent Publication No. EP 39962, U.S. patent application Ser. No. 147812/1980 (Japanese Patent Kokai No. 57-5698) proposes the adoption of a composite enzyme having both β-1,3-glucanase- and protease-activities. None of the proposed treatments with protease have, however, proved satisfactorily effective.

Among other enzymatic processes so far proposed are the utilization of a nuclease-active enzyme according to U.S. Pat. No. 4,729,958 (Japanese Patent Kokai No. 61-146193) and the purification by the action of cellulase according to U.S. Pat. No. 4,416,990 (Japanese Patent Kokai No. 57-91194). These processes also have failed to be adequately effective.

Japanese Patent No. 1318520 (Japanese Patent Kokai No. 60-44919) introduces a treatment with the simultaneous addition of lysozyme, N-acetylmuramyl-L-alanine amidase, and peptidase. These enzymes are known to be able to lyse cell walls, but they have only slight action directly on Gram negative bacteria. Despite long treatment time required, their effect is disappointingly low.

Thus, the known methods for removing water-insoluble microbial residues and culture medium-derived undissolved matter, including the methods relying upon centrifugation or cake filtration or upon enzymatic treatment to make the undissolved matter soluble in water, have not produced a satisfactory xanthan gum or solution thereof with the desired high degree of transparency.

SUMMARY OF THE INVENTION

We have discovered a new and superior method for the clarification of a xanthan gum fermented broth and aqueous solution of xanthan gum. In addition, we have discovered that particularly superior product transparency can be obtained by using X50 and X59 as the gum producing strains.

Thus, an object of the present invention is to provide a process for the preparation of xanthan gum having both excellent viscosity and transparency properties as measured by transmittance by the steps of first, heat-treating a fermentation broth containing xanthan gum or an aqueous solution of xanthan gum under specific pH and temperature conditions, thereafter treating the broth sequentially with alkaline protease and with lysozyme or vice versa, and thereafter separating solid xanthan gum by extraction from the treated broth using an organic solvent, e.g., isopropyl alcohol. An aqueous solution of 0.3 percent by weight of the solid xanthan gum thus obtained has a transparency (transmittance) of at least 80 percent as measured by the methods described herein.

In another embodiment of the invention, xanthan gum is prepared by subject strain X50 or X59 to fermentation conditions to produce a fermentation broth containing xanthan gum, and cellular and bacterial debris. The broth thus obtained is then subjected to the above described sequential heat treatment and enzymes steps. With this embodiment, it is possible to obtain xanthan gum which exhibits a transmittance of at least 75% by weight in 1.0% aqueous solution, and, preferably, at least 80% in 1.0% by weight aqueous solution. In addition, with the present invention, xanthan gum having a transmittance of at least 90% in 0.3% by weight aqueous solution can be obtained. As used herein, transmittance means the transmittance of an aqueous solution of the indicated weight percent xanthan at a wavelength of 650 nm and measured as described hereinafter.

DETAILED DESCRIPTION OF THE INVENTION

More specifically, the invention thus provides a process for preparing highly transparent fermented xanthan gum by a heat treatment at an initial pH of at least 9 and an immediately ensuing enzymatic treatment with alkaline protease and then lysozyme (or vice versa) thoroughly the solubilize water insoluble bacterial cell residues and culture medium-derived undissolved matter, without adversely affecting the viscosity properties characteristic of xanthan gum.

The heat treatment can be performed at an initial pH of from 9 to 12.5, preferably from 10 to 12, and at a temperature of from 45° to 70° C., preferably from 50° to 60° C., for at least 30 minutes. If the pH is below 9, the bacterial solubilization sometimes does not proceed efficiently, leading to unfavorable results. If it is above 12.5 the broth could be colored or the viscosity properties of the product impaired. Although the pH naturally decreases during the course of the treatment, it should preferably be maintained above 8. Any temperature below 45° C. is undesirable because it may hamper efficient solubilization of bacteria in the enzymatic treatment.

A temperature above 70° C. is again undesirable because it can cause coloring of the broth or adverse effects upon the viscosity properties of the product. Treatment for no less than 30 minutes gives a sufficient effect, but a treatment time of more than 2 hours is not advisable since it can decrease the productivity. The heat treatment must precede the enzymatic treatment. Without this pretreatment, the enzymatic treatment would not be effective or take a prolonged time period before it proves effective. However, as shown in Example 5 hereof it is possible to achieve good results at heating temperature up to 80° C. and an initial pH as low as 7.

The enzymatic treatment is carried out in two steps using alkaline protease and lysozyme. The duration of each treatment step is desirably between 20 minutes and 5 hours. A period shorter than 20 minutes is not desirable in that the treatment effect is not fully achieved. Treatment for more than 5 hours would not bring any additional treatment effect, leading to reduced productivity.

Treatment with alkaline protease is conducted at a pH in the range from 6.0 to 10.0, preferably from 7.5 to 9.0, at a concentration of 10 to 500 ppm, and at a temperature of 40° to 65° C. for at least 20 minutes. A temperature below 40° C. is not recommended from the viewpoint of productivity because lowered enzymatic activity would call for a treating time of more than 6 hours. A temperature above 65° C. would deactivate the enzyme, making the treatment non-effective. Acidity below 9 of pH 6.0 would deactivate alkaline protease, while a pH above 10.0 is also undesirable since it can deteriorate the physical properties of the product. If the concentration is below 10 ppm, a satisfactory effect would not result despite extension of the treating time. Conversely a concentration in excess of 500 ppm is not advisable because of higher production costs; an excessive concentration does not produce any further improvements.

Treatment with lysozyme is done at a pH value in the range of 5.5 to 8.0, preferably between 6.5 and 7.5, a concentration of 0.5 to 100 ppm, and a temperature of 25° to 45° C. and even up to 60° C. for at least 20 minutes. A temperature above 60° C. is undesirable because it can lower the activity of lysozyme in some cases. At a pH above 8, lysozyme would not be active and, below 5.5 the physical properties of the product could deteriorate. If the concentration is less than 0.5 ppm prolonged treatment would become necessary, and even if treatment time is prolonged it may not lead to any meaningful effects. A concentration of more than 100 ppm is not warranted from an economical standpoint. Any of the two enzymatic treatment steps may precede the other.

Enzymes useful for the reduction of the invention to practice are: an alkaline protease produced by a bacterium in the genus Bacillus, such as, *B. subtilis*, and a lysozyme known as endo-β-1,4-N-acetylhexosaminidase which hydrolyzes the β-1,4 bonds of N-acetylglucosamine and N-acetylmuramic acid in bacterial cell walls. Generally, alkaline proteases produced by *B. licheniformis*, *B. amyla-liquifaciens*, and *B. pumilis* are known besides that which originates from *B. subtilis*. As for lysozymes, there are known animal lysozymes, such as, egg white lysozymes of chickens, ducks, quails, turkeys, and geese, spleen lysozymes of dogs and rats, and lysozymes present in human urine (of leukemia patients), human milk, and tears. Plant lysozymes have been found in turnips, cabbages, and papaya juice. For the present invention, however, the origins of the enzymes are of little importance.

The process according to the invention permits the omission of such complex process steps as dilution, cake filtration, and concentration that have hitherto been required for the removal of undissolved matter. This brings ease of operation and economical advantage. A further advantage is high transparency of the product that ordinary enzymatic processes have failed to realize.

An important aspect of the present invention is our discovery that when specific hyperproducing *X. campestris* are used to generate the xanthan gum, the clarification process of the present invention yields a xanthan gum product exhibiting substantially improved transparency compared to the parent *X. campestris* strain from which they are derived. Strain X59 which is a rifampicin resistant strain and strain X50 which is a rifampicin and bacitracin resistant strain of *X. campestris* are considered hyperproducers to the extent that the strains exhibit enhanced productivity of xanthan gum as compared to strain X55 from which the hyperproducing strains are derived by a selection process as described in U.S. Pat. 5,194,386 and application Ser. No. 07/826,095. Accordingly, we have discovered a method for producing a xanthan gum broth and xanthan gum product exhibiting improved clarity as evidenced by its transparency in a 1% aqueous solution by subjecting strains X59 or X50 to submerged fermentation conditions to produce a broth of xanthan gum product. The broth thus obtained is subjected to a heat treatment as described hereinabove. Thereafter, the heat treated broth is then subjected to sequential enzymatic treatment with a protease enzyme and a lysozyme enzyme in accordance with the procedures described hereinabove. The resulting xanthan gum product may then be recovered from the broth in a conventional manner.

It should be understood, as described herein, that the inventive clarification process may be carried out on the fermentation broth, i.e., the broth after completion of the fermentation process, or, alternatively, on recovered xanthan product (i.e., in water).

DETAILED DESCRIPTION OF THE PREFERRED EMBODIMENT

The following Examples illustrates the invention.

EXAMPLE 1

| I. Preproduction medium | | II. Production medium | |
|---|---|---|---|
| Glucose | 5.8 g/l | Glucose | 58 g/l |
| Polypeptone | 5.2 " | Polypeptone | 2 " |
| Yeast extract | 2.6 " | KH$_2$PO$_4$ | 2 " |
| NaCl | 9 " | MgSO$_4$.7H$_2$O | 0.5 " |
| Water | 1.8 l | Water | 16.2 l |

A medium of composition II was placed in a 30-liter fermenter and inoculated with a *Xanthomonas campestris* broth of X59 that had been cultured for 24 hours on a medium of composition I. It was then cultured under aeration and agitation at pH 6.5 to 7.0 and at 30° C. for two days, and a broth containing 30 g xanthan gum per liter was obtained. With stirring the broth was heat-treated at an initial pH of 11° and at 55° C. for 90 minutes and, while being kept at 55° C. the broth was adjusted to pH 8.5 and, after the addition of 300 ppm alkaline protease ("Bioplase", a product of Nagase Biochemical Co.), the mixture was treated with stirring at 55° C. for two hours. Next, the resulting broth was cooled down to 35° C., 3 ppm lysozyme ("Lysozyme Taiyo", a product of Taiyo Chemical Co.) was added, and the mixture was further treated with stirring at 35° C. for one hour.

EXAMPLE 2

A broth prepared in the same way as described in Example 1 was enzymatically treated in the reverse order. After cooling, it was adjusted to pH 7.0 and, with the addition of 3 ppm lysozyme ("Lysozyme Taiyo" of Taiyo Chemical), the mixture was treated with stirring at 35° C. for two hours. Next, the broth was heated to 55° C., 300 ppm alkaline protease ("Bioplase" of Nagase Biochemical) was added, and the mixture was treated with stirring at 55° C. for one hour.

For the purposes of analysis, the broth was sampled after each of the process steps, i.e., after the conclusion of fermentation, the heat treatment, and the first and second stages of enzymatic treatment. Xanthan gum was separated by extraction from the test broth using 1.6 times by weight of isopropyl alcohol, and the extract was air dried. An aqueous solution containing 0.3 percent by weight of the thus obtained solid xanthan gum was prepared, and the sample was tested for light transmittance and viscosity (with a Brookfield viscometer at 30 rpm). Table 1 summarizes the results.

TABLE 1

| | Example 1 | | Example 2 | |
|---|---|---|---|---|
| Process Step | Transmittance | Viscosity | Transmittance | Viscosity |
| after fermentation | 11% | 290 cp | 12% | 300 cp |
| after heat treatment | 18% | 290 cp | 20% | 290 cp |
| 1st stage enzymatic treatment | 65% | 300 cp | 62% | 300 cp |
| 2nd stage enzymatic treatment | 94% | 305 cp | 94% | 300 cp |

EXAMPLES 3 and 4

The procedure of Example 1 was repeated for treatments except that the lysozyme concentration was varied. The results are given in Table 2.

TABLE 2

| | Example 3 Lysozyme 30 ppm | | Example 4 Lysozyme 1 ppm | |
|---|---|---|---|---|
| Process Step | Transmittance | Viscosity | Transmittance | Viscosity |
| after fermentation | 11% | 280 cp | 12% | 300 cp |
| after heat treatment | 18% | 290 cp | 20% | 295 cp |
| 1st stage enzymatic treatment | 65% | 290 cp | 65% | 310 cp |
| 2nd stage enzymatic treatment | 97% | 290 cp | 90% | 300 cp |

EXAMPLE 5

Fermentation performed in the same manner as in Example 1 yielded a broth containing 30 g xanthan gum per liter. With stirring, the broth at an initial pH of 7.0 was heat treated at 80° C. for 90 minutes and then cooled to and kept at 55° C. After the cooling the pH was adjusted to 8.5, and 300 ppm alkaline protease ("Bioplase" of Nagase Biochemical) was added, and the mixture was treated with stirring at 55° C. for two hours. Next, the broth was cooled down to 35° C. and after the addition of 3 ppm lysozyme ("Lysozyme Taiyo" of Taiyo Chemical), the mixture was treated with stirring at 35° C. for one hour.

For analysis, the broth was sampled after each of the process steps, i.e., after the conclusion of fermentation, the heat treatment, and the first and second stages of enzymatic treatment. Xanthan gum was separated by extraction from the test broth using 1.6 times by weight of isopropyl alcohol, and the extract was air dried. An aqueous solution containing 0.3 percent by weight of the thus obtained solid xanthan gum was prepared, and the sample was tested for light transmittance and viscosity (with a Brookfield viscometer at 30 rpm). Table 3 shows the results.

TABLE 3

| | Example 5 | |
|---|---|---|
| Process Step | Transmittance | Viscosity |
| after fermentation | 11% | 290 cp |
| after heat treatment | 8% | 275 cp |
| 1st stage enzymatic treatment | 46% | 300 cp |
| 2nd stage enzymatic treatment | 90% | 305 cp |

As shown in the above Examples, the invention procedure enables the production of xanthan gum having excellent viscosity, e.g., at least greater than about 175 cp (0.3% by weight solution with Brookfield viscometer at 30 rpm).

COMPARATIVE EXAMPLES 1 and 2

Fermentation and heat treatment were carried out in a manner similar to Example 1, and either lysozyme or alkaline protease alone was used in enzymatic treatment. The conditions for treatment with either enzyme were the same as used in Example 1. After each test period xanthan gum was separated from the resulting broth by extraction with 1.6 times by weight of isopropyl alcohol and the extract was air dried. An aqueous solution containing 0.3 percent by weight of the xanthan gum so obtained was prepared and tested for light transmittance and viscosity. As Table 4 indicates, the solutions thus prepared failed to attain, despite extended treating periods, the high transparency that the process of the present invention achieves.

TABLE 4

| Treating Time | Comparative Example 1 Lysozyme 30 ppm | | Comparative Example 2 Alkaline Protease | |
|---|---|---|---|---|
| | Transmittance | Viscosity | Transmittance | Viscosity |
| untreated | 35% | 290 cp | 35% | 290 cp |
| 2 hours | 60% | 300 cp | 62% | 300 cp |
| 4 hours | 62% | 300 cp | 65% | 300 cp |
| 6 hours | 64% | 300 cp | 69% | 300 cp |

COMPARATIVE EXAMPLE 3

In the manner described in Example 1, fermentation and heat treatment were performed, with the exception that the enzymatic treatment used lysozyme and alkaline protease together. The reaction conditions were pH 7.5 and 45° C. at which both enzymes were active. With the addition of 300 ppm Bioplase and 3 ppm lysozyme, the reaction was carried out for 6 hours. After each treating time the sample was tested for light transmittance and viscosity as was the case with Comparative Example 1. The results are given in Table 5.

TABLE 5

| | Comparative Example 3 | |
|---|---|---|
| Treating time | Transmittance | Viscosity |
| untreated | 35% | 290 cp |
| 2 hours | 63% | 310 cp |
| 4 hours | 65% | 310 cp |
| 6 hours | 69% | 310 cp |

COMPARATIVE EXAMPLE 4

The fermentation of Example 1 was directly by the two stage enzymatic treatment without the heat treatment. Samples of the individual process steps were tested for light transmittance and viscosity. Table 6, which shows the results, indicates that the omission of heat treatment reduced the enzymatic effects of the resulting broths.

TABLE 6

| | Comparative Example 4 | |
|---|---|---|
| Process step | Transmittance | Viscosity |
| after fermentation | 11% | 300 cp |
| 1st stage enzymatic treatment | 40% | 310 cp |
| 2nd stage enzymatic treatment | 60% | 310 cp |

EXAMPLE 6

A series of experiments was carried out wherein xanthan gum was produced by the submerged fermentation of strains X59 and X50. The fermentation procedures were carried out using conventional aerobic submerged fermentation techniques normally used for fermentation of *X. campestris*. The fermenter size was a 5 liter jar for these experiments.

The broths from each of the terminated fermentations were adjusted to pH 11 and then heated at 55° C. for 90 minutes. Thereafter, a series of four 200 ml aliquots from each of the resulting broths were treated as follows:

Each of the four aliquots were treated with a different system of protease and lysozyme enzymes. For this purpose the pH of the aliquot was adjusted to an appropriate pH for the particular protease. Table 7 sets forth a series of proteases commercially available and their optimum pHs and temperatures of use. Also shown is a Food Grade Lysozyme which was used in addition to the Lysozyme Taiyo used in the previous experiments.

TABLE 7

| Enzyme | Goods | Origin | Maker | Form | Optimum pH | Optimum Temp. °C. |
|---|---|---|---|---|---|---|
| Protease | 1. PTN | Trypsin | Novo | powder | 7–8 | 40–60 |
| | 2. Neutrase | Bacillus | Novo | powder | 5.5–7.5 | 45–55 |
| | 3. Protamex | Bacillus | Novo | powder | 5.5–7.5 | 40–60 |
| | 4. Flavourzyme | Aspergillus | Novo | powder | 5–7 | 45–50 |
| | 5. Multifect P-64 | Bacillus | Genencor | liquid | 6–11 | 50–60 |
| | 6. Multifect P-3000 | Bacillus | Genencor | liquid | 7–10 | 20–65 |

TABLE 7-continued

| Enzyme | Goods | Origin | Maker | Form | Optimum pH | Optimum Temp. °C. |
|---|---|---|---|---|---|---|
| Lysozyme | 1. Lysozyme (Food Grade) | egg white | Canadian lysozyme | powder | 6–7 | 30–60 |

The details of the fermentation, the final amount of xanthan gum obtained, the final cellular and the ratio of cellular debris to xanthan gum are shown in Table 8. In addition, the optical density of a 1 to 7 dilution of the initial broth, the solution obtained after the heat treatment, the solution obtained after the protease treatment, and the solution obtained after the lysozyme treatment, as well as the transmittance of a 1 wt. % solution of precipitated xanthan product obtained after the heat and enzyme treatments are shown in Table 9. The particular enzymes, temperatures and pH of the treatments used are detailed after Table 9.

TABLE 8

EFFECT OF CLARIFICATION FOR X59
Strain X59     Batch No. 555     Jar Size 5 l

FERMENTATION

| Time [Hr.] | Final XG [g/l] | Final Cell [g/l] | Residual Glu. [g/l] | Cell/XG [−] |
|---|---|---|---|---|
| 48 | 30.9 | 2.5 | 13.6 | 0.008 |

| CLARIFICATION (1/7 OD660) | Standard | New 1 | New 2 | New 3 |
|---|---|---|---|---|
| Broth | 0.739 | ← | ← | ← |
| Heat Treatment | 0.451 | ← | ← | ← |
| Protease Treatment | 0.151 | 0.213 | 0.237 | 0.166 |
| Lysozyme Treatment | 0.075 | 0.044 | 0.034 | 0.038 |
| TRANSPARENCY | | | | |
| 1 wt. % XG Transmittance [%] | 76.0 | 81.1 | 82.0 | 79.3 |
| 0.3 wt. % XG Transmittance [%] | 92.1 | 93.9 | 94.2 | 93.3 |

TABLE 9

EFFECT OF CLARIFICATION FOR X55
Strain X55     Batch No. 558     Jar Size 5 l

FERMENTATION

| Time [Hr.] | Final XG [g/l] | Final Cell [g/l] | Residual Glu. [g/l] | Cell/XG [−] |
|---|---|---|---|---|
| 48 | 21.4 | 2.5 | 18.0 | 0.12 |

| CLARIFICATION (1/7 OD660) | Standard | New 1 | New 2 | New 3 |
|---|---|---|---|---|
| Broth | 0.791 | ← | ← | ← |
| Heat Treatment | 0.427 | ← | ← | ← |
| Protease Treatment | 0.142 | 0.137 | 0.151 | 0.144 |
| Lysozyme Treatment | 0.091 | 0.073 | 0.081 | 0.066 |
| TRANSPARENCY | | | | |
| 1 wt. % XG Transmittance [%] | 48.6 | 59.9 | 52.9 | 48.9 |
| 0.3 wt. % XG Transmittance [%] | 80.5 | 85.7 | 82.6 | 80.7 |

TABLE 9-continued

EFFECT OF CLARIFICATION FOR X55
Strain X55     Batch No. 558     Jar Size 5 l

| Standard | New 1 |
|---|---|
| Bioprose 500 ppm 55° C. pH 8.5 Control 2 hr. Lys.TAIYO 3 ppm 55° C. pH 6.5 Control 1 hr. | P-64 1000 ppm 55° C. pH 8.5 Control 2 hr. Ca.Lys. 100 ppm 55° C. pH 6.5 Control 2 hr. |
| New 2 | New 3 |
| P-64 500 ppm 55° C. pH 8.5 Control 2 hr. Ca.Lys. 30ppm 55° C. pH 6.5 Control 1 hr. | PTN 200 PPM 55° C. pH 8.5 Control 2 hr Ca.Lys. 30 ppm 55° C. pH 6.5 Control 2 hr. |

For all of the experiments described herein, the transmittance was measured using a quartz cell having a cell length of 2 cm with a lightwave length of 650 nm. Measurements were made with a photoelectric colorimeter 5E-type available from Kotaki Trading. The optical density at 660 nm was measured using a cell having a cell length of 1 cm and a dilution of 7 times by weight. Measurements were made with a UV visible recording spectrophotometer UV-160 type available from Shimazu. The results of these experiments show that substantially higher clarification of broths obtained from the fermentation of X59 are obtained by the inventive treatments as compared to the broth obtained from the fermentation of X55.

In addition, these experiments show that additional enzymes, e.g., Multifect P-64 and Canadian Lysozyme perform as well as the standard enzymes Bioplase and Lysozyme Taiyo. Preferred enzymatic treatment conditions for Multifect P-64 and Canadian Lysozyme are shown in Table 10. It is noted that pH adjustments were carried out with either 10% aqueous sulfuric acid or 20% aqueous sodium hydroxide depending on whether the pH needed to be decreased or increased. In addition, the protease "Bioplase", which is a produce of Nagase Biochemical Co., is commercially obtained as a powder absorbed or disbursed on calcium carbonate. Thus, for use, the powder is mixed with water resulting in dissolution of the enzyme into the aqueous phase. The calcium carbonate is separated from the aqueous phase and it is the aqueous phase which is used. In addition, all concentrations of enzymes are indicated as the concentration in the solution to which they are added, e.g., 500 ppm of enzymes means that in the aliquot or broth, the concentration of enzyme in solution for the treatment was 500 ppm.

TABLE 10

ENZYMATIC TREATMENT CONDITION

| | Protease | Lysozyme |
|---|---|---|
| Goods Condition | Multifect P-64 (Genencor) | Food Grade Lysozyme (Canadian Lysozyme) |

TABLE 10-continued

| ENZYMATIC TREATMENT CONDITION | | |
|---|---|---|
| Addition | 500 ppm | 30 ppm |
| pH | pH 8.5 Control | pH 6.5 Control |
| Temp. | 55° C. | 55° C. |
| Time | 2 hr. | 1 hr. |

A series of fermentations using X59, X50 and X55 were carried out: Example 8
Media 1

| Seed Media | | Production Media | |
|---|---|---|---|
| Glucose | 5.8 g/l | Glucose | 58 g/l |
| Polypeptone | 5.2 g/l | Polypeptone | 2.0 g/l |
| Yeast extract | 2.6 g/l | KH$_2$PO$_4$ | 2.0 g/l |
| NaCl | 9.0 g/l | MgSO$_4$.7H$_2$O | 0.5 g/l |
| Water | 1.8 l | Water | 16.2 l |

Strain X55 was used. A production media was placed in a 30 liter fermenter and inoculated with a *Xanthornonas campestris* broth that had been cultured for 24 hours in seed media. It was then cultured under aeration and agitation at pH 6.5 to 7.0 and at 30° C. for two days, and a broth containing 20 g xanthan gum per liter was obtained. The broth was heat-treated with stirring at an initial pH of 11 and at 55° C. for 90 minutes and while being kept at 55° C., the broth was adjusted to pH 8.5 with 10% aqueous H$_2$SO$_4$. After the addition of supernatant of an aqueous solution of 9.0 g (500 ppm) alkaline protease; "Bioplase" a product of Nagase Biochemical Co., the mixture was heated with stirring at 55° C. for two hours. Next, the pH was adjusted to 6.5 and an aqueous solution of 0.054 g (3 ppm) lysozyme "Lysozyme Taiyo", a product of Taiyo Chemical Co., was added. The mixture was heated with stirring at 55° C. for one hour.

EXAMPLE 9

The procedure of Example 1 was repeated except that protease Multifect P-64, a product of Genencor, was used in place of Bioplase and lysozyme "Canadian Lysozyme", a product of Food Grade Lysozyme, was used in place of Lysozyme Taiyo.

EXAMPLE 10

The procedure of Example 1 was repeated except that strain X59 was used in place of X55.

EXAMPLE 11

The procedure of Example 1 was repeated except that strain X59 was used in place of X55, protease "Multifect P-64" was used in place of Bioplase and lysozyme "Canadian Lysozyme" was used in place of Lysozyme Taiyo.

EXAMPLE 12

The procedure of Example 1 was repeated except that strain X50 was used in place of X55.

EXAMPLE 13

The procedure of Example 1 was repeated except that strain X59 was used in place of X55 and Media 2 was used in place of Media 1.

Media 2

| Seed Media | | Production Media | |
|---|---|---|---|
| Glucose | 5.8 g/l | Glucose | 58 g/l |
| Polypeptone | 5.2 g/l | NH$_4$NO$_3$ | 1.7 g/l |
| Yeast extract | 2.6 g/l | KH$_2$PO$_4$ | 2.0 g/l |
| NaCl | 9.0 g/l | MgSO$_4$.7H$_2$O | 0.5 g/l |
| Water | 1.8 l | Water | 16.2 l |

EXAMPLE 14

The procedure of Example 1 was repeated except that strain X50 was used in place of X55 and that Media 2 was used in place of Media 1.

EXAMPLE 15

A broth was prepared used in strain X59 in place of X55 in the same way as described in Example 1. The resulting broth was enzymatically treated in the reverse order, that is, after heat-treatment, it was adjusted to pH 6.5 and, after the addition of aqueous solution of 0.054 g (3 ppm) lysozyme, "Lysozyme Taiyo", the mixture was heated with stirring at 55° C. for one hour. Next, a supernatant of aqueous solution of 9.0 g (500 ppm) alkaline protease "Bioplase" was added and the mixture was heated with stirring at 55° C. for two hours.

The enzyme treatments used in the above experiments are characterized hereafter as Method A and Method B.

Method A

Heat treatment: initial pH 11, 90 minutes
Protease treatment: 500 ppm, pH 8.5, 55° C., 120 minutes ("Bioplase", a product of Nagase Biochemical Co.)
Lysozyme Treatment: 3 ppm, pH 6.5, 55° C., 60 minutes ("Lysozyme Taiyo", a product of Taiyo Chemical Co.)

Method B

Heat Treatment: initial pH 11, 90 minutes
Protease treatment: 550 ppm, pH 8.5, 55° C., 120 minutes ("Multifect P-64", a product of Genencor)
Lysozyme treatment: 30 ppm, pH 6.5, 55° C., 60 minutes ("Canadian Lysozyme", a product of Food Grade Lysozyme).

As shown in Table 11, broths and xanthan gum produced from strains X59 and X50 exhibit substantially superior transmittance using the inventive procedure as compared to the original strain X55.

TABLE 11

| Strain | X55 | X55 | X59 | X59 | X50 |
|---|---|---|---|---|---|
| Example | 8 | 9 | 10 | 11 | 12 |
| Media | media1 | media1 | media1 | media1 | media1 |
| Fermentation Result | | | | | |
| Time [Hr] | 48 | 48 | 48 | 48 | 48 |
| Final XG [g/L] | 21.4 | 22.1 | 29.5 | 30.9 | 28.8 |
| Final Cell [g/L] | 2.5 | 2.6 | 1.9 | 2.5 | 2.2 |
| Residual Glu. [g/L] | 18.0 | 18.4 | 10.5 | 13.6 | 5.6 |

TABLE 11-continued

OD660 of diluted broth

| Enzyme treatment | A | B | A | B | A |
|---|---|---|---|---|---|
| Broth | 0.791 | 0.883 | 0.658 | 0.739 | 0.912 |
| Heat treatment | 0.427 | 0.455 | 0.315 | 0.451 | 0.334 |
| Protease treatment | 0.142 | 0.136 | 0.100 | 0.237 | 0.098 |
| Lysozyme treatment | 0.091 | 0.072 | 0.046 | 0.034 | 0.028 |

Transmittance [%]

| | | | | | |
|---|---|---|---|---|---|
| 1% XG aqueous solution | 48.6 | 58.9 | 87.1 | 82.0 | 85.9 |
| 0.3% XG aqueous solution | 80.5 | 85.3 | 95.9 | 94.2 | 95.5 |
| Strain | X59 | X50 | Strain | | X59 |
| Example | 13 | 14 | Example | | 15 |
| Media | media2 | media2 | Media | | media1 |

Fermentation Result

| Time [Hr] | 48 | 48 | Time [Hr] | | 48 |
|---|---|---|---|---|---|
| Final XG [g/L] | 34.6 | 29.4 | Final XG [g/L] | | 28.6 |
| Final Cell [g/L] | 2.1 | 3.4 | Final Cell [g/L] | | 2.1 |
| Residual Glu. [g/L] | 0.8 | 0.0 | Residual Glu. [g/L] | | 8.3 |

OD660 of diluted broth

| Enzyme treatment | A | A | Enzyme treatment | | A (reverse) |
|---|---|---|---|---|---|
| Broth | 0.856 | 1.298 | Broth | | 0.672 |
| Heat treatment | 0.454 | 0.494 | Heat treatment | | 0.344 |
| Protease treatment | 0.168 | 0.128 | Protease treatment | | 0.226 |
| Lysozyme treatment | 0.068 | 0.037 | Lysozyme treatment | | 0.032 |

Transmittance [%]

| 1% XG aqueous solution | 80.9 | 83.3 | 1% XG aqueous solution | | 83.3 |
|---|---|---|---|---|---|
| 0.3% XG aqueous solution | 93.8 | 94.7 | 0.3% XG aqueous solution | | 94.7 |

We claim:

1. A process for the preparation of purified xanthan gum, comprising:

a) subjecting strain ATCC 55429 or ATCC 55298 to submerged fermentation conditions to produce a fermentation broth containing xanthan gum and cellular debris;

b) heating the fermentation broth obtained from step a) at a temperature from 45° to 80° C. for a period of at least 30 minutes at an initial pH of 7 to 12.5;

c) contacting the heated broth from step b) with an alkaline protease for a period of from 20 minutes to five hours;

d) contacting the broth from step b) with lysozyme for a period of from 20 minutes to five hours; and e) recovering the xanthan gum from the broth from step d).

2. A process for the preparation of xanthan gum having high transmittance in aqueous solution, comprising:

a) subjecting strain ATCC 55429 or ATCC 55298 to submerged fermentation conditions to produce a fermentation broth containing xanthan gum and cellular debris;

b) heating the fermentation broth obtained from step a) at a temperature from 45° to 80° C. for a period of at least 30 minutes at an initial pH of 7 to 12.5;

c) contacting the heated broth from step b) with lysozyme for a period of from 20 minutes to five hours;

d) contacting the broth from step c) with an alkaline protease for a period of from 20 minutes to five hours; and e) recovering the xanthan gum from the broth from step d).

3. The process of claim 1 or 2 wherein the temperature of the heating step is from 45° C. to 70° C. and the initial pH is from 9 to 12.5.

4. The process of claim 1 or 2 wherein the contacting with alkaline protease is carried out by the addition of 10 to 500 ppm of alkaline protease to the fermented broth at a temperature of 40° to 65° C. and a pH of 6.0 to 10.0 for at least 30 minutes.

5. The process of claim 1 or 2 wherein the contacting with the lysozyme is carried out by the addition of 0.5 to 100 ppm of the lysozyme to the fermented broth at a temperature of 25° to 45° C. and a pH of 5.5 to 8.0 for at least 30 minutes.

6. The process of claim 1 or 2 wherein the xanthan gum recovered has a transmittance of at least 75% in 1% by weight aqueous solution.

7. The process of claim 1 or 2 wherein the xanthan gum recovered has a transmittance of at least 80% in 1% by weight aqueous solution.

8. The process of claim 1 or 2 wherein the xanthan gum recovered has a transmittance of at least 90% in 0.3% by weight aqueous solution.

* * * * *